United States Patent [19]

Giles et al.

[11] 4,331,680

[45] May 25, 1982

[54] PESTICIDAL COMPOUNDS, COMPOSITIONS AND METHODS

[75] Inventors: David P. Giles, Loughborough; John C. Kerry, Edwalton; Antonin Kozlik, Clifton; Bryan H. Palmer, Burton Joyce; Stephen W. Shutler, Hucknall; Robert J. Willis, Carlton, all of England

[73] Assignee: The Boots Company, Nottingham, England

[21] Appl. No.: 181,278

[22] Filed: Aug. 25, 1980

[30] Foreign Application Priority Data

Aug. 31, 1979 [GB] United Kingdom ................ 7930356

[51] Int. Cl.$^3$ .................. A61K 31/255; C07C 143/68

[52] U.S. Cl. .................... 424/303; 546/226; 546/264; 260/923; 546/284; 546/330; 260/465 E; 546/331; 260/465 D; 546/332; 548/112; 260/456 A; 548/193; 548/194; 260/456 F; 548/197; 548/230; 260/453.99; 548/255; 548/266; 542/412; 549/8; 549/59; 542/417; 549/60; 549/62; 542/424; 549/64; 549/75; 542/425; 549/77; 560/12; 544/57; 560/13; 560/27; 544/58.1; 560/38; 560/39; 544/58.4; 560/140; 560/142; 544/58.6; 564/35; 564/36; 544/58.7; 564/38; 564/81; 544/59; 564/154; 564/155; 544/60; 564/226; 564/228; 544/130; 564/251; 424/200; 544/131; 424/202; 424/203; 544/152; 424/206; 424/210; 544/157; 424/211; 424/246; 544/159; 424/248.4; 424/248.5; 544/160; 424/248.54; 424/248.55; 544/163; 424/248.56; 424/263; 544/164; 424/267; 424/269; 546/22; 424/274; 424/275; 546/188; 424/285; 424/300; 546/189; 424/304; 424/309; 546/209; 424/321; 424/322; 546/222; 424/323; 424/324; 546/223; 424/325; 424/326; 546/225; 548/413; 548/557

[58] Field of Search .................. 260/326.41, 326.5 L, 260/326.62, 326.82, 326.83, 326.85, 326.86, 347.2, 347.3, 347.4, 347.5, 347.7, 453.99, 456 A, 456 F, 465 D, 465 E, 923; 542/412, 417, 424, 425; 544/57, 58.1, 58.4, 58.6, 58.7, 59, 60, 130, 131, 152, 157, 159, 160, 163, 164; 546/22, 188, 189, 209, 222, 223, 225, 226, 264, 284, 330, 331, 332; 548/112, 193, 194, 197, 230, 255, 266; 549/8, 59, 60, 62, 65, 75, 77; 560/12, 13, 27, 38, 39, 140, 142; 564/35, 36, 38, 81, 154, 155, 226, 228.25; 424/303

[56] References Cited

U.S. PATENT DOCUMENTS 3,414,650 12/1968 Catino et al. .......................... 564/81
3,732,307 5/1973 Middleton .......................... 564/251
3,912,779 10/1975 Tarnow et al. ....................... 564/81

*Primary Examiner*—Nicky Chan
*Attorney, Agent, or Firm*—Lawrence Rosen

[57] ABSTRACT

Novel compounds are described which are substituted benzophenone hydrazones. They have pesticidal activity, especially against insects and acarids, and pesticidal compositions and methods are described. Methods of making the compounds, and novel intermediates, are also described.

11 Claims, No Drawings

PESTICIDAL COMPOUNDS, COMPOSITIONS AND METHODS

This invention relates to compounds having pesticidal activity.

Commercially available insecticidal products generally fall into four main categories, namely chlorinated compounds such as DDT, camphechlor and BHC, organophosphorus compounds such as parathion, carbamates such as carbaryl and, more recently, synthetic pyrethroids such as permethrin.

Resistance to an insecticide often develops after a period of use and there is therefore always a need for new insecticides and particularly for new groups of insecticides.

Many proposals appear in the literature that a group of compounds has pesticidal properties, but often such compounds are found not to be commercially acceptable as pesticides.

We have now found that certain benzophenone hydrazones have insecticidal activity against a wide range of pests.

Certain benzophenone hydrazones are already known. For instance in U.S. Pat. No. 3,732,307 there are described compounds of the formula:

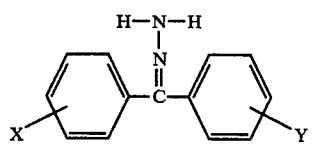

wherein
X is selected from the group consisting of perfluoroalkyl, perfluoroalkoxy and perfluoroalkylthio containing up to four carbon atoms, and
Y is selected from the group consisting of hydrogen, chlorine, bromine, fluorine, alkyl, alkoxy, alkylthio, perfluoroalkyl, perfluoroalkoxy and perfluoroalkylthio containing up to four carbon atoms.

These compounds are distinguished in that specification from, for example, benzophenone hydrazones described by J. R. DoAmaral et. al., J. Med. Chem. 12,21 (1969) apparently by virtue of, inter alia, having the hydrazone $NH_2$ unsubstituted in the compounds of U.S. Pat. No. 3,732,307. The compounds of that specification are described primarily as plant growth regulants although it is also mentioned in U.S. Pat. No. 3,732,307 that the compounds have activity against insects.

We have now found that certain hydrazones containing substituents other than those described for X and Y have valuable insecticidal properties.

According to the invention there are provided compounds of formula I

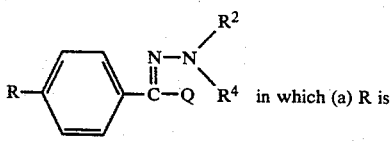 in which (a) R is

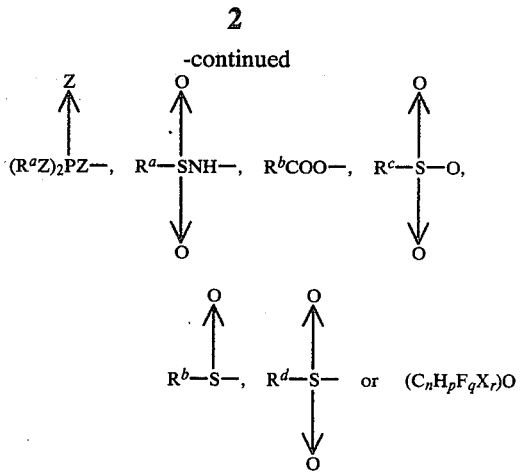

where $R^a$ is optionally substituted alkyl or aryl, $R^b$ is optionally substituted alkyl, $R^c$ is fluorine, p-nitrophenyl, 3,5-di(trifluoromethyl)phenyl or aryloxy, $R^d$ is monoalkylamino, n is 1 to 3, p is at least 1, q is at least 1, r is 0 to $2n-1$, $p+q+r=2n+1$, X is halogen other than fluorine, and Z is oxygen or sulphur;

$R^2$ and $R^4$ may be the same or different and are hydrogen, alkyl, acyl, an ester or thioester group, optionally substituted carbamoyl, optionally substituted alkylsulphonyl, arylsulphonyl, N-substituted iminoalkyl, optionally substituted alkenyl, optionally substituted alkynyl, heteroaryl, substituted alkyl or

where $R^a$ and Z have the meanings given above; or $R^2$ and $R^4$ together with the nitrogen to which they are attached form a 5 to 7 membered ring which may optionally contain one or more heteroatoms, or $R^2$ and $R^4$ together form the group $=CR^5R^6$, where $R^5$ and $R^6$ may be the same or different and are hydrogen, optionally substituted alkyl, optionally substituted cycloalkyl, optionally substituted alkenyl, optionally substituted alkoxy, optionally substituted amino, optionally substituted alkenyloxy, aryloxy or aryl, or $R^5$ and $R^6$ together with the carbon to which they are attached form a ring which may optionally contain one or more heteroatoms; and Q is a phenyl group optionally substituted by one or more groups selected from halogen, alkyl, haloalkyl, alkoxy, aryloxy, aryl, aralkyl, alkenyl and cyano, or is hydrogen, optionally substituted alkyl or cycloalkyl or (b) R is $R^3SO_2O-$ where $R^3$ is optionally substituted alkyl, alkenyl, N,N-dialkylamino or phenyl optionally substituted by alkyl or halogen; and (i) one of $R^2$ and $R^4$ is optionally substituted alkylsulphonyl, arylsulphonyl, N-substituted iminoalkyl, optionally substituted alkenyl, optionally substituted alkynyl, substituted alkyl, heteroaryl or

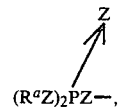

where $R^a$ and Z have the meanings given above; and the other has the meaning given under (a) above for a single group, or $R^2$ and $R^4$ together form the group $=CR^5R^6$, where $R^5$ and $R^6$ have the meanings given under (a) above, and Q has the definition given in (a) above or (ii) $R^2$ and $R^4$ may be the same or different and are hydrogen, alkyl, acyl, an ester or thioester group, optionally substituted carbamoyl, optionally substituted thiocarbamoyl or $R^2$ and $R^4$ together with the nitrogen to which they are attached form a 5 to 7 membered ring which may optionally contain one or more heteroatoms and Q is a phenyl group having at least one substituent selected from aryloxy, aralkyl, alkenyl and cyano and optionally one or more substituents selected from halogen, alkyl, haloalkyl and alkoxy, or is hydrogen, optionally substituted alkyl or cycloalkyl.

A preferred group of compounds of the invention are compounds of formula I wherein

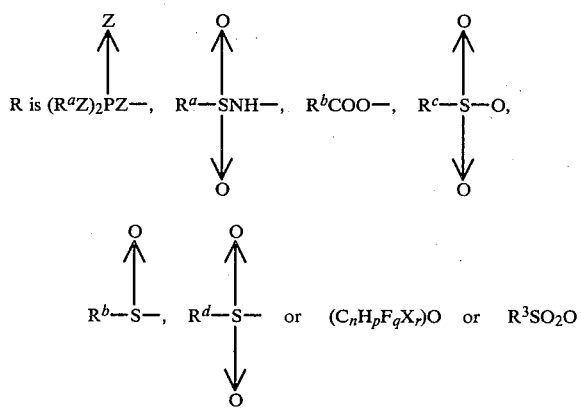

where $R^a$ is optionally substituted alkyl or aryl, $R^b$ is optionally substituted alkyl, $R^c$ is fluorine, p-nitrophenyl, 3,5-di(trifluoromethyl)phenyl or aryloxy, $R^d$ is monoalkylamine, n is 1 to 3, p is at least 1, q is at least 1, r is 0 to $2n-1$, $p+q+r=2n+1$, X is halogen other than fluorine, $R^3$ is optionally substituted alkyl, alkenyl, N,N-dialkylamine or phenyl optionally substituted by alkyl or halogen, and Z is oxygen or sulphur and $R^2$ and $R^4$ together form the group $=CR^5R^6$, where $R^5$ and $R^6$ may be the same or different and are hydrogen, optionally substituted alkyl, optionally substituted cycloalkyl, optionally substituted alkenyl, optionally substituted alkoxy, optionally substituted amino, optionally substituted alkenyloxy, aryloxy or aryl, or $R^5$ and $R^6$ together with the carbon to which they are attached form a ring which may optionally contain one or more heteroatoms; and Q is a phenyl group optionally substituted by one or more groups selected from halogen, alkyl, haloalkyl, alkoxy, aryloxy, aryl, aralkyl, alkenyl and cyano, or is hydrogen, optionally substituted alkyl or cycloalkyl.

Any alkyl, alkenyl, alkynyl, alkoxy or alkenyloxy groups are generally $C_{1-4}$. If they are substituted, suitable substituents include halo, phenyl, phenoxy, cyano, alkylamino and alkoxycarbonyl and for alkyl the substituents may include also alkyl. Preferred substituents for particular groups are given in more detail below.

In the present specification any references to halo or halogen should be construed as a reference to fluorine, chlorine, bromine or iodine, preferably fluorine, chlorine or bromine.

In Formula I, Q is preferably a monosubstituted phenyl group with the substituent preferably in the 4-position and is especially 4-halophenyl, e.g., 4-chlorophenyl. Examples of other substituents include trifluoromethyl, phenyl, phenoxy, vinyl and cyano. When Q is optionally substituted alkyl, this is preferably $C_{1-4}$ alkyl.

R is preferably methylsulphonyloxy or trifluoromethylsulphonyloxy. When R is a group containing a substituent $R^b$ this is preferably $C_{1-4}$ alkyl e.g. methyl or ethyl.

When $R^2$ and $R^4$ form the group $=CR^5R^6$, $R^5$ and $R^6$ are preferably hydrogen, $C_{1-4}$ alkyl or $C_{1-4}$ alkoxy. Generally one of $R^5$ and $R^6$ is not hydrogen. Other suitable groups include $C_{3-6}$ cycloalkyl, which may be substituted e.g. by $C_{1-4}$ alkyl; aryl, e.g. phenyl, pyridyl and thienyl; and alkenyl, e.g. allyl. Where $R^5$ or $R^6$ is substituted alkyl, the substituents may be e.g. halo, phenyl, phenoxy, cyano, alkylamino or alkoxycarbonyl. If $R^5$ and $R^6$ form a ring, this ring is preferably a 4 to 7-membered ring which may be substituted and may be unsaturated. Suitable substituents include $C_{1-4}$ alkyl, or two substituents may together form a fused second ring. If one of $R^5$ and $R^6$ is substituted amino this may be for example mono- or dialkylamino or monocycloalkylamino.

If $R^2$ and $R^4$ do not form this group then $R^2$ is preferably hydrogen and $R^4$ is preferably other than hydrogen and is usually a carbonyl derivative. When $R^2$ or $R^4$ are alkyl this may be, e.g. of 1 to 4 carbon atoms and is preferably methyl. When $R^2$ or $R^4$ is N-substituted iminoalkyl this may be, for example N-aryliminomethyl where aryl may be for example 2,4-dimethylphenyl. If $R^2$ or $R^4$ form a ring with the nitrogen to which they are attached this may be for example piperidine, pyrrolidine, thiamorpholine, triazole, morpholine and especially 2-oxazolidinone. If $R^2$ or $R^4$ are an ester or thioester group this is generally of formula $R^8XCO$, where X is oxygen or sulphur, preferably oxygen and $R^8$ is an organic radical e.g. alkyl, e.g. of 1 to 12, preferably 1 to 8 carbon atoms, and especially ethyl, these alkyl groups being optionally substituted, (e.g. by $C_{1-4}$ alkoxy; $C_{3-7}$ cycloalkyl; halogen; cyano; aryl, such as phenyl, substituted phenyl or naphthyl; or aryloxy, such as phenoxy and substituted phenoxy); cycloalkyl; e.g. of 3 to 7 carbon atoms and especially cyclopentyl; alkenyl e.g. of 2 to 12 carbon atoms, which group may optionally be substituted (e.g. by aryl such as phenyl or substituted phenyl); alkynyl e.g. of 2 to 6 carbon atoms; aryl such as optionally substituted phenyl or 2-naphthyl; heteroaryl, such as furyl, thienyl, pyridyl, and heterocyclyl such as morpholinyl, piperidyl and thiamorpholinyl. Where a phenyl group is substituted this may be by a wide number of groups e.g. $C_{1-4}$ alkyl, $C_{1-4}$ haloalkyl, nitro, $C_{1-4}$ alkoxy, $C_{1-4}$ alkylthio, $C_{1-4}$ dialkylamino, phenyl or halogen. If $R^2$ or $R^4$ are acyl this is generally of formula $R^9CO$ where $R^9$ is $R^8$ as defined above or hydrogen.

If $R^2$ or $R^4$, in Formula I, is a carbamoyl group, the group may be of the formula $-CNR^{10}R^{11}$ where $R^{10}$ and $R^{11}$ are the same or different and are hydrogen, optionally substituted alkyl or optionally substituted phenyl or together with the nitrogen to which they are attached form a 5 or 7 membered ring which may optionally contain one or more heteroatoms. Suitable optionally substituted alkyl or phenyl or heterocyclic groups are listed above in the description of, for instance, $R^2$, $R^4$ and $R^8$.

A particularly valuable group of compounds are those in which R is trifluoromethylsulphonyloxy or methanesulphonyloxy, Q is 4-chlorophenyl and $R^2$ and $R^4$ form the group $=CR^5R^6$ where one of $R^5$ and $R^6$ is hydrogen or $C_{1-4}$ alkyl and the other is $C_{1-4}$ alkoxy. These compounds generally have a broader spectrum of activity than compounds for instance where $R^2$ and $R^4$ have other meanings. They are also more soluble in common organic solvents thus enabling the formation of more concentrated compositions which is a particularly important commercial and practical consideration. Another valuable group of compounds are those where R and Q are as above and $R^5$ and $R^6$ are optionally substituted alkyl or cycloalkyl or together form a ring. These latter compounds generally have a higher activity against aphids than compounds where $R^2$ and $R^4$ have other meanings.

The compounds of the invention are active against a variety of economically important insects that cause serious and widespread damage to crops such as for example, insects of the order Lepidoptera including caterpillars of the diamond back moth (*Plutella xylostella*), the cabbage white butterfly (*Pieris brassicae*), the Egyptian cotton leaf worm (*Spodoptera littoralis*) and Heliothis spp. such as *H.armigera*, *H.viriscens* and *H.zea*. Many of the compounds have also shown activity against other caterpillars such as these of the codling moth (*Laspeyresia pomonella*). Some of the compounds have shown activity against other pests such as beetles of the order Colcoptera, including the mustard beetle (*Phaedon cochleariae*), grain weevil (*Sitophilus granarius*), flour beetle (*Tribolium castaneum*) and mealworm (*Tenebrio molitor*); cockroaches of the order Dictyoptera such as *Blatella germanica;* aphids of the order Hemiptera, including the vetch aphid (*Megoura viciae*).

Many of the compounds also have activity against a variety of economically important acarid and insect pests of animals, including farm livestock. For example, many compounds have been shown to be active against larvae stages of insects of the order Diptera e.g. sheep blowfly (Lucilia spp.) and mosquitoes e.g. *Aedes aegypti*. Some of the compounds, especially those in which $R^6$ is alkoxy and $R^5$ is hydrogen, have shown systemic activity, i.e. the internal tissues of an animal which has been treated with the compound exert an insecticidal effect. This property is important in the treatment of animals such as cattle, which are infested with tissue-dwelling stages of insects e.g. warble fly (Hypoderma spp.). Some of the compounds are also active against lice and keds and acarid parasites, especially ticks, e.g. *Boophilus microplus*, and mites, e.g. Sarcoptes spp.

Some of the compounds have also been shown to have nematicidal, fungicidal, herbicidal and plant-growth regulant activity.

The invention also includes an insecticidal composition comprising a compound of formula I and an inert diluent. More than one compound of the invention can be included in the composition, and the diluent can be a solid or liquid, optionally together with a surface active agent, for example a dispersing agent, emulsifying agent or wetting agent.

One or more additional pesticides such as, for example, compounds known to possess acaricidal or insecticidal activity can be added to the composition of the invention to enhance or widen the spectrum of its activity.

Such additional pesticides include, for example, an organophosphorus compound such as tetrachlorvinphos, fenitrothion, demeton-S-methyl, phosalone, dioxathion, chlorfenvinphos, dichlorvos, bromophosethyl, diazinon, dimethoate, methyl parathion, sulprofos, fenthion, trichlorphon, coumaphos, dialifos or chlorpyrifos; a carbamate such as methomyl, carbaryl, pirimicarb or promecarb; a bridged diphenyl compound such as tetradifon, tetrasul or DDT; a chlorinated hydrocarbon such as benzene hexachloride, endosulphan, endrin or toxaphene; an acaricide such as amitraz, chlordimefon, clenpyrin, chlormethiuron or nimidane; a synthetic pyrethroid such as permethrin, fenvalerate, NRDC 161, or cypermethrin; or a tin pesticide such as cyhexatin or fenbutatin oxide.

The composition of the invention can take any of the forms known for the formulation of insecticidal compounds; for example, it can be in the form of a solution, an aqueous dispersion, an aqueous emulsion, an emulsifiable concentrate, a dispersible powder, a dusting powder or granules. Thus it can be in a suitable form for direct application as an insecticide or as a concentrate requiring dilution with an appropriate quantity of water or other diluent before application.

As a dispersion the composition comprises a compound of the invention dispersed in an aqueous medium. It is often convenient to supply the consumer with a concentrate which when diluted with water forms a dispersion of the desired concentration and can be provided in, for example, any of the following forms. It can be a dispersible solution which comprises a compound of the invention dissolved in a water-miscible solvent with the addition of a dispersing agent, or a dispersible powder comprising a compound of the invention and a dispersing agent. A further alternative comprises a compound of the invention in the form of a finely ground powder in association with a dispersing agent and intimately mixed with water to give a paste or cream which can if desired be added to an emulsion of oil in water to give a dispersion of active ingredient in an aqueous oil emulsion.

An emulsion comprises a compound of the invention dissolved in a water-immiscible solvent which is formed into an emulsion with water in the presence of an emulsifying agent. An emulsion of the desired concentration can be formed from a concentrated stock emulsion that comprises a compound of the invention in combination with an emulsifying agent, water and water-immiscible solvent. Alternatively the consumer can be supplied with an emulsifiable concentrate comprising a solution of a compound of the invention in a water-immiscible solvent containing an emulsifying agent.

A dusting powder comprises a compound of the invention intimately mixed and ground with a solid pulverant diluent, for example, kaolin.

A granular solid comprises a compound of the invention associated with similar diluents to those employed in dusting powders but the mixture is granulated by known methods. Alternatively the active ingredient can be absorbed or adsorbed on a pre-formed granular diluent for example fuller's earth, attapulgite or limestone grit.

The concentration of the active ingredient (when used as the sole active component) in a composition for direct application to the crop by conventional ground methods is preferably within the range of 0.001 to 10 percent by weight of the composition, especially 0.005 to 5 percent by weight, but more concentrated compositions containing up to 20 percent may be desirable in the case of aerial sprays. As a concentrated primary composition the concentration of active ingredients may vary widely and can be, for example, from 5 to 95 percent by weight of the composition.

As previously described the compounds of the invention have exceptional activity as insecticides and accordingly the invention includes a method of combating insects which comprises applying a compound of formula I to the locus of the insects, that is, the insects or their habitat. The compound of the invention can either be applied on its own or more preferably as one of the compositions described above.

Many of the insects which the compounds of the invention are active against, for example those of the order Lepidoptera and Coleoptera, attack plant life and a preferred method of the invention is one of the protecting plants from attack by insects by applying a compound of formula 1 to the locus of the plants. For instance the diamond back moth and cabbage white butterfly attack vegetable crops such as brassicas, and leaf worms are a serious pest on cotton.

Direct treatment by for example spraying or dusting the plants infested with insects is often the preferred method but the active compound can also be applied to the soil in which plants are grown as granules, or as a root drench. In such instances the active compound is absorbed by the roots of the plant and confers protection from the insects. The quantity of active compound applied can vary widely depending on the particular circumstances and usually the amount is in the range of from 0.01 to 20 kilogram per hectare, more especially, from 0.1 to 10 kilogram per hectare.

Also included in the invention is a method of protecting animals from attack by pests which comprises treating the animal with a compound of formula I. Parasites are a frequent source of irritation to animals such as livestock and many can be controlled by external application of a compound of formula I. The method may be by direct application to the animals, or by application to the quarters, e.g. buildings, in which the animals live.

The compounds of the invention can be prepared by a number of processes, as follows:

(1) By reacting a compound of formula II

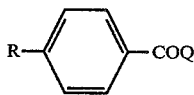

with a compound of formula $NH_2NR^2R^4$. When $R^2$ and $R^4$ are both hydrogen the product can then be acylated with (a) an acyl halide or acid anhydride when $R^2$ or $R^4$ is to is to be any acyl group, with (b) a chloroformate or chlorothioformate when $R^2$ or $R^4$ is to be an ester group, with (c) an isocyanate when $R^2$ or $R^4$ is to be a carbamoyl (d) a sulphonyl halide when $R^2$ or $R^4$ is to be an alkyl or arylsulphonyl group (e) a formimidate when $R^2$ or $R^4$ is to be an aryliminomethyl compound or (f) when $R^2$ and $R^4$ together are to form $=CR^5R^6$ with (i) a compound of formula $O=CR^5R^6$ when $R^5$ and $R^6$ are both not alkoxy or (ii) a compound of formula $(R^5)_3R^6C$ when at least $R^5$ is alkoxy, or a compound of formula $R^5R^6C(O\ alkyl)_2$ when one of $R^5$ and $R^6$ is substituted amino.

Compounds in which one of $R^5$ or $R^6$ alkoxy can be reacted with a substituted amine to form a compound in which one of $R^5$ or $R^6$ is a substituted amino group.

In this specification it will be appreciated that the term "acylating agent" includes all these types of reagent.

The reaction with the hydrazine or hydrazine derivative is usually carried out at a temperature of from 50° C. to 100° C., in the presence of acetic acid or a salt of an organic base and a strong acid e.g. pyridinium chloride.

The acylation reaction is preferably carried out in the presence of an inert organic liquid as the reaction medium which is also preferably a solvent for the reactants, at a temperature of from 0° C. to 100° C. Advantageously the reaction is effected in the presence of a suitably acid-binding agent, for example a tertiary alkylamine, pyridine or an alkali metal carbonate. When the acylating agent is a halide this is preferably the chlorine, Some of the compounds of formula II are novel and can be prepared by reacting a compound of formula III

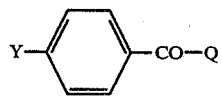

in which Y is OH, SH or $NH_2$ when R is an oxy, thio or substituted amino group, respectively with a compound of formula $R^eX$ where $R^e$ is R minus the oxy, thio or amino group and X is halogen or, when R is $R^bCOO$, X may also be hydroxy.

This step is preferably carried out in the presence of any inert organic solvent and an acid binding agent.

When R is $R^dSO_2-$, Y can be $SO_2Cl$ and compound III reacted with $R^dH$ to give compound II.

(2) By reacting a compound of formula IV

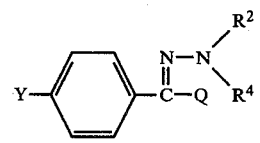

in which $R^2$ and $R^4$ are not both hydrogen with a compound of formula $R^eX$, where Y, $R^e$ and X have the meanings given above. The reaction is preferably carried out at a temperature of 0° to 100° C., usually in the presence of an acid binder.

Compounds of formula IV can, in their turn, be prepared by reacting a suitable hydrazine derivative of the formula $NH_2NR^2R^4$ with a compound of formula III above, preferably in the presence of an inert organic solvent and optionally together with acetic acid or a salt of an organic base and a strong acid, e.g. pyridinium chloride.

In many cases one compound of the invention may be converted by a suitable analogy process into a second compound of the invention. For instance, compounds in which one of $R^5$ and $R^6$ is alkoxy can be reacted with an amino group to convert the alkoxy into a substituted amino group.

The present state of our knowledge indicates that most of the above reactions give rise to product that comprises a mixture of the E and Z-isomers.

It is to be understood that formula I above denoting the compounds of the invention includes both of these isomers. In all cases the pairs of isomers can be separated by conventional methods, such as for example chromatography or fractional recrystallisation, but, as the isomeric mixtures have very valuable insecticidal activity, we generally find that there is no advantage in separating the isomers. The activity of the isomers of any one compound may differ and in some cases the activity of one isomer may be negligible; pure isomers lacking insecticidal activity form no part of the present invention.

It will be appreciated that particularly when treating animal pests the products can be administered in a substantial release formulation. Thus the compound may be incorporated in a suitable polymer which may be attached to the animal in the form of an ear tag, collar, leg band etc., or it may be administered as a bolus or implant.

If desired animals may be treated by injection, oral drench or with a pour-on formulation.

The invention is illustrated in the following Examples. The structures of compounds were confirmed by elementary and other appropriate analyses.

EXAMPLES 1–42

Phenol is reacted with p-chlorobenzoyl chloride in a Friedel-Crafts reaction in the presence of aluminium chloride to give 4-chloro-4′-hydroxybenzophenone, m.p. 179°–181° C. (A). To a solution of this (5 g.) in pyridine (6 ml.) was added methanesulphonyl chloride (2.5 g.), at room temperature. The reactants were heated on a steam bath for 1½ hours and the liquid reaction product poured into dilute hydrochloric acid to give a solid which was filtered and air-dried. This solid was recrystallised from industrial methylated spirits to give 4-chloro-4′-methylsulphonyloxybenzophenone, m.p. 120°–121° C. (B). To a solution of this (9.35 g.) in ethanol (200 ml.) was added hydrazine hydrate (8 ml.) followed by glacial acetic acid (1.5 ml.). The mixture was heated under reflux with stirring for 17 hours. The solvent was evaporated under reduced pressure to give an oil which was extracted with chloroform. The extract was washed with water, aqueous sodium hydroxide and water and then dried over magnesium sulphate. The solvent was evaporated under reduced pressure to give an oil. On standing this crystallised to give 4-chloro-4′-methylsulphonyloxybenzophenone hydrazone, m.p. 70°–110° C. (C). This product (5 g.) was heated under reflux with acetone (25 ml.) for 24 hours. The mixture was then evaporated under reduced pressure to give 4-chloro-4′-methylsulphonyloxybenzophenone isopropylidenehydrazone m.p. 148°–9° C.

In a similar manner using the appropriate starting materials and ketones or aldehydes, the products of Table 1 were obtained. In Example 43, (C) was reacted with 3-amino crotononitrile in acetic acid.

TABLE I

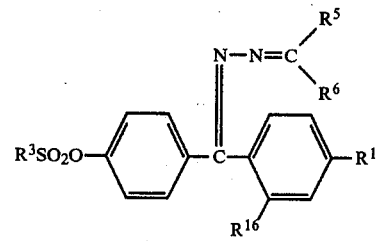

| Ex. No. | R$^1$ | R$^{16}$ | R$^3$ | R$^5$ | R$^6$ | m.p. (°C.) |
|---|---|---|---|---|---|---|
| 2 | Cl | H | Me | Me | Et | 110.5–111.5 |
| 3 | Cl | H | Me | H | Ph | 135–137 |
| 4 | Cl | H | Me | Me | CF$_3$ | 103–105 |
| 5 | Cl | H | CF$_3$ | Me | Me | Oil |
| 6 | Cl | H | Me | | together are —(CH$_2$)$_5$— | 106.5–115 |
| 7 | Cl | Cl | Me | Me | Me | Oil |
| 8 | Br | H | Me | Me | Me | 140–142 |
| 9 | Cl | H | Me | | together are —(CH$_2$)$_4$— | 130–131 |
| 10 | Cl | H | Me | | together are —(CH$_2$)$_6$— | 89–90 |
| 11 | Cl | H | Me | | together are —CH=CH(CH$_2$)$_3$— | 165–175 |
| 12 | Cl | H | Me | Me | CH$_2$COOEt | 157–158 |
| 13 | Cl | H | Me | Me | CH$_2$COOMe | 139–140 |
| 14 | Cl | H | Me | Me | Pr$^i$ | 90–92 |
| 15 | Cl | H | Me | | together are —CH(Me)—(CH$_2$)$_4$— | 112–115 |
| 16 | Cl | H | Me | Me | Bu$^i$ | Oil |
| 17 | Cl | H | CF$_3$ | | together are —(CH$_2$)$_6$— | 105.5–106.5 |
| 18 | Cl | H | Me | Me | —CH$_2$CH$_2$Ph | Oil |
| 19 | Cl | H | Me | | together are —CH$_2$CH(Me)—(CH$_2$)$_3$— | Oil |
| 20 | Cl | H | Me | Me | —CH$_2$CH=CH$_2$ | Oil |
| 21 | Cl | H | Me | Me | —CH$_2$OPh | Oil |
| 22 | Cl | H | Me | | together are CH$_2$—CH—CH(CH$_2$)$_2$— (cyclohexyl) | Oil |
| 23 | Cl | H | Me | Me | —CH$_2$F | 111.5–112.5 |
| 24 | Cl | H | CF$_3$ | | together are CH$_2$CH(Me)(CH$_2$)$_3$— | Oil |
| 25 | Cl | H | Me | Me | CH$_2$NMe$_2$ | Oil |
| 26 | Cl | H | Me | | together are —(CH$_2$)$_2$CH(Me)(CH$_2$)$_2$— | Oil |
| 27 | Cl | H | Me | | together are —CH$_2$CH(Me)(CH$_2$)$_2$— | 120–121 |
| 28 | Cl | H | Me | | together are —(CH$_2$)$_3$— | 171–172 |
| 29 | Cl | H | Me | Me | Bu$^t$ | 72–73 |
| 30 | Cl | H | Me | Me | cyclopropyl | 99–102 |
| 31 | Cl | H | Me | | cyclopropyl-cyclopropyl | 158–160 |
| 32 | Cl | H | CF$_3$ | Me | cyclopropyl | Oil |
| 33 | Cl | H | Me | Me | —CH$_2$Ph | Oil |
| 34 | Cl | H | Me | Me | cyclohexyl | 88–98 |

TABLE I-continued

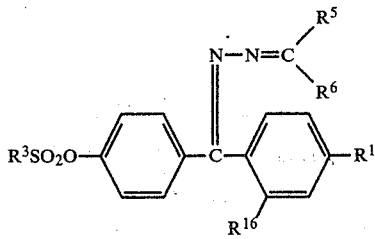

| Ex. No. | R¹ | R¹⁶ | R³ | R⁵ | R⁶ | m.p. (°C.) |
|---|---|---|---|---|---|---|
| 35 | Cl | H | Me | Me | Ph (cyclopropyl-Ph) | Oil |
| 36 | Cl | H | Me | Me | Me (cyclopropyl-Me) | Oil |
| 37 | Cl | H | Me | Me | (thienyl) | Oil |
| 38 | Cl | H | Me | H | (pyridyl) | 114–115 |
| 39 | Cl | H | CF₃ | Me | (cyclobutyl) | Oil |
| 40 | CF₃ | H | CF₃ | Me | Me | 60–62 |
| 41 | Cl | H | CF₃ | together are —CH=CH(CH₂)₃— | | Oil |
| 42 | Cl | H | Me₂N | Me | Me | Oil |
| 43 | Cl | H | Me | Me | CH₂CN | 134–135 |

The intermediates in Examples 5, 7, 8, 17, 24, 32, 39, 40, 41 and 42 had melting points as follows:

| Ex. No. | Type A | Type B | Type C |
|---|---|---|---|
| 5,17,24,32, 39, and 41 | 179–181 | 57–60 | 84–99 |
| 7 | 134–135 | 119–120 | Oil |
| 8 | 187.5–191 | 135–136.5 | 110–113 |
| 40 | 136–138 | 42–44 | 123–124.5 |
| 42 | 179–181 | 81.5–82.5 | 110–116.5 |

EXAMPLES 44–57A

Pyridinium chloride (0.05 g.) was added to a solution of C from Example 1 (20 g.) in triethyl orthoformate (50 ml.) and the mixture heated on a steam bath for 8 hours. Ethanol which formed was distilled off as it was produced. The mixture was treated with charcoal, filtered and evaporated under reduced pressure to give an oil which on trituration with ethanol solidified and the resulting product was recrystallised from ethanol to give ethyl N-(4-chlorophenyl-4-methylsulphonyloxyphenylmethylene)formohydrazonate, m.p. 104°–107° C.

In a similar manner the appropriate intermediate C was reacted with various esters or acetals to give products as follows.

TABLE II

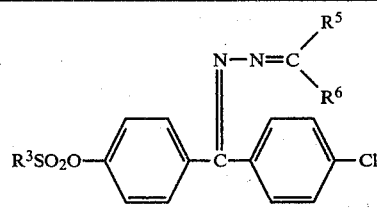

| Ex. No. | Ester or acetate. | R³ | R⁵ | R⁶ | m.p. (°C.) |
|---|---|---|---|---|---|
| 45 | (EtO)₃CMe | Me | Me | OEt | 109–112 |
| 46 | (PrO)₃CH | Me | H | OPr | 128–130 |
| 47 | (EtO)₃CEt¹ | Me | Et | OEt | 94–99 |
| 48 | (MeO)₃CBu¹ | Me | Bu | OMe | 94–95 |
| 49 | (EtO)₃CH² | CF₃ | H | OEt | 58–69 |
| 50 | (EtO)₃CEt¹ | CF₃ | Et | OEt | Oil |
| 51 | (Pr^iO)₃CH² | CF₃ | H | OPr^i | Oil |
| 52 | (EtO)₃CMe | CF₃ | Me | OEt | Oil |
| 53 | (EtO)₃CMe | Me₂N | Me | OEt | 104–105 |
| 54 | (CH₂=CHCH₂O)₃CH | CF₃ | H | CH₂=CHCH₂O— | Oil |
| 55 | (PrO)₃CH | CF₃ | H | OPr | Oil |
| 56 | Me₂NCH(OEt)₂¹ | Me | H | NMe₂ | 162–170 |
| 57 | Me₂NCH(OEt)₂¹ | CF₃ | H | NMe₂ | 133 |

¹No pyridinium hydrochloride used
²Acetic acid replaced the pyridinium hydrochloride.

EXAMPLES 57B AND 57C

A solution of product of Example 47 (10 g.) in n-butylamine (25 ml.) was refluxed for 24 hours. After treatment with charcoal, excess n-butylamine was distilled and the product subjected to vaccum to give N'''-butyl-N-(4'-chlorophenyl-4-methylsulphonyloxyphenylmethylene)propioamidrazone, as a clear oily liquid.

In a similar manner but replacing the n-butylamine with cyclopropylamine and heating in a sealed tube, there was obtained N-(4'-chlorophenyl-4-methylsulphonyloxyphenylmethylene-N'''-cyclopropylpropioamidrazone, as an oil.

EXAMPLE 57D

A solution of concentrated sulphuric acid (0.05 ml) in trimethyl orthoformate (5 ml) was added to a solution of intermediate C from Example 5 (10 g) in trimethyl orthoformate (50 ml) and the mixture heated for 10 hours on a steam bath. Methanol was allowed to distil as it was formed and the mixture then boiled for 3 hours during which time further methanol was distilled through a column. Excess trimethyl orthoformate was then distilled and the residue was extracted with light petroleum (b.p. 60°–80° C.) and the extract worked up in conventional manner to give methyl-N-(4-chlorophenyl-4-trifluoromethylsulfphenyloxyphenylmethylene)-formohydrazonate, obtained as an oil.

In a similar manner to Example 44, but omitting the pyridinium hydrochloride, methyl N-2,4-dimethylphenylformimidate gave 4-chloro-4'-methylsulphonyloxybenzophenone 2,4-dimethylphenyliminomethylhydrazone, as a glass like solid (Example 58) and ethyl N-4-chloro-2-methylphenylformimidate gave 4-chloro-4'-methylsulphonyloxybenzophenone 4-chloro-2-methylphenyliminomethylhydrazone m.p. 60–>100° C. (Example 59).

EXAMPLES 60–65

In a similar manner to that described in Example 1, the various 4-substituted 4'-hydroxybenzophenones (Intermediates A) were formed and converted to the corresponding 4'-methylsulphonylbenzophenones (Intermediates B). These (6 g.) were then heated under reflux with ethyl carbazate (4.3 g.) in ethanol (86 ml.) for 24 hours. The mixtures were then evaporated under reduced pressure and dissolved in dichloromethane. These solutions were washed with water, aqueous sodium hydroxide, water, dilute hydrochloric acid and evaporated under reduced pressure to give the products shown in the following table.

TABLE III

MeSO$_2$O—〈ph〉—C(=NNHCOOEt)—〈ph〉—R, R$^1$

| Ex. No. | R | R$^1$ | m.p. of product (°C.) | m.p. of intermediate A | m.p. of intermediate B |
|---|---|---|---|---|---|
| 60 | —OPh | H | Resin | 140 | 144–146 |
| 61 | —CH=CH$_2$ | H | Resin | 97–99 | 97–98 |
| 62 | —CH Ph | H | Resin | 134.5–135.5 | 85.5–87 |
| 63 | —Ph | H | Oil | 176.5–180 | 139–140 |
| 64 | —CN | H | 105–107.5 | 180–184* | 119–120 |
| 65 | —Cl | CN | 155–156 | 120–121* | 120–121 |

*Prepared from corresponding bromo compound by reaction with cuprous cyanide in dimethyl formamide and extraction with dichloromethane.

EXAMPLES 66–68

4-Amino-4'-chlorobenzophenone (4 g.) was heated under reflux with a mixture of pyridine (15 ml.) and methanesulphonyl chloride (10 g.) for 30 mins. The mixture was then poured into a mixture of ice and hydrochloric acid and then filtered to give 4-chloro-4'-methylsulphonylaminobenzophenone m.p. 198°–200° C. A mixture of this product (2.4 g.) ethyl carbazate (2 g.) and a trace amount of pyridine hydrochloride in ethanol (50 ml.) was heated under reflux for 24 hours. The mixture was then cooled to 0° C. and filtered to give 4-chloro-4'-methylsulphonylaminobenzophenone ethoxycarbonyl hydrazone, m.p. 198°–200° C.

In a similar manner there was also obtained 4-chloro-4'-phenylsulphonylaminobenzophenone m.p. 183°–184° C. which gave 4-chloro-4'-phenylsulphonylaminobenzophenone ethylcarbonylhydrazone m.p. 238°–240° C. (Example 67); and 4-chloro-4'-ethoxycarbonylaminobenzophenone, m.p. 171°–172° C. (from ethyl chloroformate) which gave 4-chloro-4'-ethoxycarbonylaminobenzophenone ethoxycarbonylhydrazone, m.p. 228°–229° C. (Example 68).

EXAMPLES 69–73

A mixture of 4-hydroxyacetophenone (7.8 g.) methyl carbazate (5.5 g.), ethanol (100 ml.) and glacial acetic acid (1.5 ml.) was heated under reflux for 24 hours. The mixture was cooled, filtered and the product dried to give 4-hydroxyacetophenone methoxycarbonylhydrazone, m.p. 209°–212° C. (Intermediate F). A solution of trifluoromethanesulphonyl chloride (8.58 g.) in tetrahydrofuran (20 ml.) was added dropwise with stirring to a solution of F (9.62 g.) in triethylamine (11.5 ml.) cooled to 0° C. over 25 minutes. The mixture was stirred overnight at room temperature. The mixture was poured into water and filtered and the product recrystallised from industrial methylated spirits to give 4-trifluoromethylsulphonyloxyacetophenone methoxycarbonylhydrazone, m.p. 135°–137° C.

In a similar manner starting from the appropriate 4-hydroxyacetophenone or 4-hydroxybenzaldehyde type F intermediates were formed using ethyl carbazate instead of methyl carbazate for which the corresponding 4-trifluoromethylsulphonyl compounds were formed as shown in Table IV.

TABLE IV

CF$_3$SO$_2$O—〈ph〉—C(=NNHCOOEt)—R$^{14}$

| Ex. No. | R$^{14}$ | m.p. (°C.) | m.p. of type F intermediate (°C.) |
|---|---|---|---|
| 70 | Et | 106–110 | 144–148 |
| 71 | Me | 131–133 | 177–179 |
| 72 | H | 124—127 | 214–218 |
| 73 | ⊲ (cyclopropyl) | 91–93 | 162–164 |

EXAMPLES 74–77

A solution of A from Example 1 (92.8 g.) ethyl carbazate (100 g.) and glacial acetic acid (100 ml.) in ethanol (1 liter) was heated under reflux, with stirring, for 48 hours. Evaporation of solvent under reduced pressure gave a slurry and the solid was separated from the liquors by filtration. This solid was washed with a little cold industrial methylated spirit and then dried in vacuo at 50° C.

The liquors were evaporated again under reduced pressure and the resulting oil was extracted with chloroform and the extract washed with aqueous sodium carbonate and then water. The extract was dried over magnesium sulphate and evaporated under reduced pressure to give a second batch of solid.

The combined solid material was recrystallised from industrial methylated spirits to give 4-chloro-4'-hydroxybenzophenone ethoxycarbonylhydrazone, mp. 185°–187° C. (E). To a solution of (E) (19.2 g.) in dry pyridine (150 ml) cooled to 0° C. was added cooled sulphuryl chloride fluoride (10 g.) over 30 minutes. The mixture was stirred at 0° C. for 3 hours and then for 1 hour at 40° C. The mixture was poured into a mixture of ice and dilute hydrochloric acid and then extracted with ether. The extract was dried and evaporated to dryness to give a glass-like product which was purified on an alumina column to give 4'-chloro-4'-fluorosulphonyloxybenzophenone ethoxycarbonylhydrazone, obtained as a glass, whose structure was confirmed by mass spectrometry.

In a similar manner starting from E and using the appropriate chloride there was obtained 4-chloro-4'-(4-nitrophenylsulphonyloxy)benzophenone ethoxycarbonyl hydrazone, m.p. 141°–7° C. (Example 75); 4-chloro-4'-[3,5-di(trifluoromethyl)phenylsulphonyloxy]benzophenone ethoxycarbonylhydrazone, m.p. 134°–8° recrystallisation of the evaporated reaction mass from isopropanol.

EXAMPLES 78–93

In a similar manner to that described in Example 1 intermediate A or related 4'-substituted-4-hydroxybenzophenones were reacted with various chloro compounds in a similar manner to that described in Example 1 to give type B intermediate. These were then treated with hydrazine or hydrazine derivatives in a similar manner to that described in Example 60 to give the following products.

TABLE V

| Ex. No. | R | $R^1$ | $R^2$ | $R^4$ | mp. of product(°C.) | mp of B (°C.) |
|---|---|---|---|---|---|---|
| 78 | Cl–⟨⟩–OSO$_2$O— | Cl | COOEt | H | 100–116 | 101–102 |
| 79 | Cl–⟨⟩–OSO$_2$O— | Cl | H | H | 87.5 | 101–102 |
| 80 | MeNHS(O)(O)— | Cl | COOEt | H | 154–160 | 132–134 |
| 81 | EtNHS(O)(O)— | Cl | COOEt | H | 170–180 | 112–114 |
| 82 | Cl$_2$CHCF$_2$O— | Cl | COOEt | H | 105–118 | 78.5–81 |
| 83 | Cl$_2$CHCF$_2$O— | Cl | H | H | Oil | 78.5–81 |
| 84 | CF$_2$HO— | Cl | COOEt | H | 89–91 | 85–86.5 |
| 85 | CF$_2$HO— | Cl | CO$_2$CH$_2$CCl$_3$ | H | 100–114 | 85–86.5 |
| 86 | Cl$_2$CHCF$_2$O— | CF$_3$ | COOEt | H | 96–136 | 74–76 |
| 87 | PrS(O)— | Cl | COOEt | H | 131–149 | 106–108 |
| 88 | MeS(O)— | Cl | COOEt | H | 155–162 | 134–135.5 |
| 89 | Cl$_2$CHCF$_2$O— | Cl | —COO(CH$_2$)$_2$— | | 121–129 | 78.5–81 |
| 90 | MeSO$_2$O— | Cl | (thiazol-Me) | H | 192–193 | 120–121 |
| 91 | Cl$_2$CHCF$_2$O— | F | COOEt | H | 117–132 | 55–57 |
| 92 | Cl$_2$CHCF$_2$O— | MeO | COOEt | H | 115–123 | 96–98 |
| 93 | CF$_2$HO | Cl | H | H | Oil | 85–86.5 |

(Example 76); and 4-chloro-4'-(2,2,2-trifluoroethoxycarbonyloxy)benzophenone ethoxycarbonylhydrazone, m.p. 115°–117° C. (Example 77). In the case of Example 75 the pyridine was replaced by a mixture of triethylamine and tetrahydrofuran and the product obtained by recrystallisation of the evaporated reaction mixture from n-butanol. In the case of Example 76 the pyridine was replaced by a mixture of triethylamine and 4-dimethylaminopyridine and the product obtained by The hydrazine derivatives used were as follows:
ethyl carbazate—Examples 78,80,81,82,86,87,88,91 and 92
hydrazine hydrate—Examples 79,83,84 and 93
2,2,2-trichloroethyl carbazate—Example 85
3-amino-2-oxazolidine—Example 89
4-methylthiazol-2-yl hydrazine—Example 90

The chloro compounds used were as follows:
p-chlorophenyl chlorosulphate—Examples 78 and 79
N-methylsulphamoyl chloride—Example 80

N-ethylsulphamoyl chloride—Example 81
1,1-difluoro-1,2,2-trichloroethane—Example 82,83,86,89,91 and 92
chlorodifluoromethane—Examples 84, 85 and 93
methanesulphonyl chloride—Example 90

In Examples 87 and 88 intermediate B was prepared by a Friedel-Crafts reaction between 4-chlorobenzoyl chloride and the appropriate alkylthiobenzene to give the benzophenone followed by oxidation with hydrogen peroxide.

In Examples 91-93 the 4'-hydroxybenzophenone was converted to its sodium derivative by reaction with sodium hydroxide before treatment with the chloro compound.

EXAMPLE 94

In a similar manner to Example 78 4-hydroxyacetophenone was converted to 4-(2,2-dichloro-1,1-difluoroethoxy) acetophenone, obtained as a liquid which on treatment with ethyl carbazate gave the corresponding ethoxycarbonylhydrazone m.p. 166°-168° C.

EXAMPLE 95

Methanesulphonyl chloride (3.78 g.) in dry ether (15 ml.) was added dropwise over 30 minutes to intermediate C from Example 1 (9.75 g.) in dry pyridine (20 ml.). The mixture was kept at below $-5°$ C. and maintained at this temperature with stirring for a further 30 minutes and then stirred overnight at room temperature. It was then poured into water and extracted with chloroform. The extract was washed with hydrochloric acid (5 N) and water, dried and evaporated to dryness under reduced pressure. The product was recrystallised from industrial methylated spirits to give 4-chloro-4'-methylsulphonyloxybenzophenonemethylsulphonylhydrazone, m.p. 160°-165°.

In a similar manner starting from the appropriate hydrazone and using the appropriate sulphonyl chloride the following compounds were also obtained.

TABLE VI $R^3SO_2O-\langle\text{phenyl}\rangle-C(=NNHSO_2R^{13})-\langle\text{phenyl}\rangle-Cl$

| Ex. No. | $R^3$ | $R^{13}$ | m.p. (°C.) |
|---|---|---|---|
| 96 | Me | Ph | 193–194.5 |
| 97 | Me | Pr | 140–143 |
| 98 | Me | —⟨phenyl⟩—Bu$^t$ | 195–200.5 |
| 99 | Me | —CH$_2$Cl | 127–130 |
| 100* | CF$_3$ | Me | 131–144 |
| 101 | Me | Et | 112–120 |
| 102* | CF$_3$ | Ph | 135.5–138.5 |
| 103 | Me | —⟨phenyl⟩—Cl | 198–200 |
| 104 | Me | —⟨phenyl⟩—Me | 176–177 |
| 105 | Me | —⟨phenyl⟩—NO$_2$ | 179–181 |
| 106* | CF$_3$ | —⟨phenyl⟩—Me | 108.5–115 |

*Starting material was Intermediate C from Example 5.

EXAMPLES 107-109

To the product of Example 83 (6.1 g) in pyridine (20 ml) was added dropwise with stirring a solution of benzoyl chloride (2.47 g) in ether (15 ml.) and stirring continued overnight. Water was added and the mixture worked up in conventional manner to give 4-chloro-4'-(2,2-dichloro-1,1-difluoroethoxy)benzophenone benzoylhydrazone, m.p. 121°-122° C.

In a similar manner but replacing the benzoyl chloride with 2,2,2-trichloroethylchloroformate there was obtained 4-chloro-4'-(2,2-dichloro-1,1-difluoroethoxy)-benzophenone 2,2,2-trichloroethoxycarbonylhydrazone, m.p. 97°-103° C. (Example 108).

In a similar manner the product of Example 93 and butyryl chloride gave 4-chloro-4'-difluoromethoxybenzophenone butyrylhydrazone m.p. 114°-125° C. (Example 109).

EXAMPLE 10

A mixture of the product of Example 47 (10 g) and ammonium chloride (1.32 g) in methanol (150 ml) was refluxed for 20 hours. The mixture was cooled and filtered and the precipitate recrystallised from ethanol to give 1,7-di(4-chlorophenyl)-4-ethyl-1,7-di-(4-methylsulphonyloxyphenyl)-2,3,5,6-tetraazahepta-1,3,6-triene, m.p. 184°-5° C.

EXAMPLE 111

A solution of intermediate B from Example 1 in ethanol was refluxed with a mixture of hydrazine hydrate and glacial acetic acid and the mixture then worked up in conventional manner to give 4-chloro-4'-methylsulphonyloxybenzophenone hydrazone. This was then converted to the corresponding ethoxycarbonyl hydrazone by reaction with acetyl chloride in the presence of pyridine. The product was separated into its geometric isomers by high pressure liquid phase chromatography. The E-isomer (2 g.) in dry ether was refluxed for 100 hours with a mixture of allyl bromide (1.21 g.) and 50% sodium hydroxide (0.48 g.). Ether was added and the mixture filtered and evaporated. The residue was extracted with light petroleum (b.p. 62°-68° C.) and evaporated to give (E)-4-chloro-4'-methylsulphonyloxybenzophenone N-allyl-N-ethoxycarbonylhydrazone, obtained as an oil.

EXAMPLES 112-113

A mixture of E from Example 74 (5 g.) potassium carbonate (4.3 g.) and diethylchlorophosphate (4.5 ml.) in acetone (50 ml.) was heated under reflux for 24 hours. The mixture was then poured into water (150 ml.) and extracted with dichloromethane. The extract was dried, evaporated to dryness and the residue distilled under reduced pressure to give 4-chloro-4'-(diethoxyphosphinyloxy)benzophenone ethoxycarbonylhydrazone, obtained as an oil.

In a similar manner using diethylchloromonothiophosphate, there was obtained 4-chloro-4'(diethoxyphosphinothioyloxy) benzophenone ethoxycarbonylhydrazone m.p. 106°-106.5° C.

EXAMPLE 114

N-(2,4-dimethylphenyl)-N'-methylformamidine (2.9 g.) was added to a warm solution of the product of Example 44 (6.7 g.) in isopropanol (30 ml.). The mixture was heated on a steam bath for 15 mins and then evaporated in vacuo. The residual oil was heated on a steam bath for a further 24 hours. Isopropanol was added and oil which separated on cooling was collected and evaporated in vacuo to give 4-chlorophenyl-(4-methylsulphonyloxyphenyl)methylene N-(2,4-dimethylphenyliminomethyl)-N-methylformamidehydrazone, as a glass-like solid.

EXAMPLE 115

A solution of C from Example 1 (10 g) in pyridine (20 ml) was mixed with diethylchlorophosphate (4.9 ml) and a trace of dimethylaminopyridine and the mixture stirred for 24 hours at room temperature. It was then extracted with dichloromethane and the extract evaporated to dryness. The oil which remained was subjected to thin layer chromatography to give 4-chloro-4'-methylsulphonyloxybenzophenone diethoxyphosphinylhydrazone, m.p. 90°–91° C.

EXAMPLE 116

Propionic acid (3.9 ml) and trifluoroacetic anhydride (5.6 ml) were heated together at 60° C. for 5 minutes. To this was added E (9.56 g) from Example 74, portionwise, and the mixture heated at 60° C. for 40 minutes and then allowed to cool for one hour. The mixture was then poured into aqueous sodium bicarbonate and extracted with chloroform. The extract was washed with aqueous sodium bicarbonate and water, dried and evaporated to dryness under reduced pressure. The residue was triturated with light petroleum (b.p. 62°–68° C.) to give a solid which on recrystallisation from methylene dichloride/light petroleum (b.p. 40°–60° C.) gave 4-chloro-4'-propionyloxybenzophenone ethoxycarbonylhydrazone m.p. 120°–146°.

EXAMPLE 117

The following types of compositions were formulated as below:

| | w/v (%) |
|---|---|
| Water dispersible concentrate | |
| Product of Example 1 | 8 |
| Sopraphor S25[1] | 3 |
| Sopraphor S70[2] | 2 |
| N-Methylpyrrolidone | to 100 |
| Emulsifiable concentrate | |
| Product of Example 45 | 12.5 |
| Atlox 4851 B[3] | 1.5 |
| Atlox 4855 B[3] | 3.5 |
| Esso 200[4] | to 100 |
| Emulsifiable concentrate | |
| Product of Example 49 | 30 |
| Atlox 4851B[3] | 5 |
| Atlox 4855B[3] | 5 |
| Xylene | to 100 |
| Seed Dressing | |
| Product of Example 49 | 10 |
| Dowanol DPM[5] | to 100 |

[1]Ethoxylated polyarylphenol
[2]Calcium alkylarylsulphonate
[3]Blends of calcium dodecylbenzenesulphonate and a triglyceride ethoxylate.
[4]High boiling aromatic solvent
[5]Dipropylene glycol methyl ether

EXAMPLE 118

This Example illustrates the activity of compounds of the invention against larvae of the diamond back moth (*Plutella xylostella*).

Ten larvae were placed in a small container together with a square inch of cabbage which had been dipped in the test solution and allowed to dry. After twenty-four hours, untreated cabbage was added for food and, after a further twenty-four hours, an assessment was made of the mortality of the larvae.

Two replicates were carried out for each test compound and test solutions of varying concentrations employed so that an $LD_{50}$ value could be calculated.

The compounds of Examples 1 to 52, 56, 57A, B and C, 58–82, 84–89, 90, 94–107 and 110–116 had an $LD_{50}$ of less than 5000 ppm.

We claim:

1. Compounds of formula I $$R-\!\!\left\langle\!\!\bigcirc\!\!\right\rangle\!\!-\!\!\overset{N-N}{\underset{\parallel}{C}}\!\!-\!\!\overset{R^2}{\underset{R^4}{<}} \quad I$$

in which Q is p-halophenyl or p-trifluoromethylphenyl and R is $R^3SO_2O$ where $R^3$ is alkyl or haloalkyl and $R^2$ and $R^4$ together form the group $=CR^5R^6$, where $R^5$ and $R^6$ may be the same or different and are hydrogen, alkyl, alkenyl, alkoxy, alkenyloxy groups (which groups, other than hydrogen, may be optionally substituted by halo, phenyl, phenoxy, cyano, alkylamino or alkoxycarbonyl) monoalkylamino, dialkylamino, monocycloalkyloamino, cycloalkyl (optionally substituted by $C_{1-4}$ alkyl), phenyl, phenoxy, pyridyl or thienyl or $R^5$ and $R^6$ together with the carbon to which they are attached form a 4–7 carbon membered ring, which may optionally be unsaturated and may optionally be substituted by alkyl or by two substituents which form a fused 6-membered ring.

2. Compounds according to claim 1 in which Q is 4-chlorophenyl.

3. Compounds according to claims 1 or 2 in which R is methylsulphonyloxy or trifluoromethylsulphonyloxy.

4. Compounds according to claim 1 in which R is trifluoromethylsulphonyloxy or methanesulphonyloxy, Q is 4-chlorophenyl and $R^2$ and $R^4$ form the group $=CR^5R^6$ where one of $R^5$ and $R^6$ is hydrogen or $C_{1-4}$ alkyl and the other is $C_{1-4}$ alkoxy.

5. A compound according to claim 1 which is ethyl N-(4-chlorophenyl-4-trifluoromethylsulphonyloxyphenylmethylene)formohydrazonate.

6. A compound according to claim 1 which is ethyl N-(4-chlorophenyl-4-trifluoromethylsulphonylxyphenylmethylene)acetohydrazonate.

7. A compound according to claim 1 which is methyl N-(4-chlorophenyl-4-trifluoromethylsulphonyloxyphenylmethylene)formohydrazonate.

8. An insecticidal composition comprising an effective amount of a compound according to claim 1 and an inert diluent or carrier.

9. A composition according to claim 8 in which the compound is a compound wherein R is trifluoromethylsulphonyloxy or methanesulphonyloxy, Q is 4-chlorophenyl and $R^2$ and $R^4$ form the group $=CR^5R^6$ where one of $R^5$ and $R^6$ is hydrogen or $C_{1-4}$ alkyl and the other is $C_{1-4}$ alkoxy.

10. A method of combating insects which comprise applying an effective amount of a compound according to claim 1 to the locus of the insects.

11. A method according to claim 10 wherein the locus is a plant or an animal.

* * * * *